US006302853B1

(12) United States Patent
Sak (10) Patent No.: US 6,302,853 B1
(45) Date of Patent: Oct. 16, 2001

(54) METHOD AND APPARATUS FOR SAMPLING CERVICAL TISSUE

(75) Inventor: Robert F. Sak, Ft. Pierce, FL (US)

(73) Assignee: R & G Medical And Development Corp., Boca Raton, FL (US)

( * ) Notice: Subject to any disclaimer, the term of this patent is extended or adjusted under 35 U.S.C. 154(b) by 0 days.

(21) Appl. No.: 09/512,258

(22) Filed: Feb. 24, 2000

(51) Int. Cl.$^7$ .................................................. A61B 10/00
(52) U.S. Cl. ............................................................ 600/569
(58) Field of Search ..................................... 600/569, 572, 600/581

(56) References Cited

U.S. PATENT DOCUMENTS

| | | |
|---|---|---|
| 2,767,703 | 10/1956 | Nieburgs . |
| 3,776,219 | 12/1973 | Brown . |
| 3,995,618 | 12/1976 | Kingsley et al. . |
| 4,157,709 | 6/1979 | Schuster et al. . |
| 4,586,604 | 5/1986 | Alter . |
| 4,628,941 | 12/1986 | Kosasky . |
| 4,784,158 | 11/1988 | Okimoto . |
| 4,788,985 | 12/1988 | Manning et al. . |
| 4,862,899 | 9/1989 | Bucaro . |
| 4,877,037 | 10/1989 | Ko et al. . |
| 5,121,752 | 6/1992 | Canna . |
| 5,251,641 | * 10/1993 | Xavier .................................. 600/567 |
| 5,449,071 | 9/1995 | Levy . |
| 5,787,891 | 8/1998 | Sak . |

OTHER PUBLICATIONS

"New Devices Aim At Improving Pap Test Accuracy", pp. 1–5, Reprint of Oct. 1996 *FDA Consumer*.
"The Wallach Papette Full Spectrum Cervical Cell Collector", Wallach Surgical Devices, Inc., pp. 1–2, 1999.

* cited by examiner

Primary Examiner—Robert L. Nasser
Assistant Examiner—Pamela L. Wingood
(74) Attorney, Agent, or Firm—Banner & Witcoff, Ltd.

(57) ABSTRACT

A cervical sampling system for collecting a cervical sample for a Pap test. The cervical sampling system includes an insertion tube and an introduction guide member that guides the insertion tube into a vaginal cavity. The vaginal insertion tube includes an insertion depth indicator to allow the user to determine the appropriate depth to insert the tube. A cervical sampler is positioned within the vaginal insertion tube and extends into the vaginal cavity to collect samples. The insertion tube and cervical sampler include signaling members which cooperate to indicate to the user when the cervical sample has been rotated through a complete revolution.

47 Claims, 5 Drawing Sheets

METHOD AND APPARATUS FOR SAMPLING CERVICAL TISSUE

FIELD OF INVENTION

The present invention relates to an improved apparatus and system for obtaining a sample of cervical tissue and/or vaginal secretions such that developing cancerous cells may be detected. The present invention also relates to an improved method of using the sampling apparatus to collect such samples.

BACKGROUND

Unlike many cancers that cause pain, noticeable lumps, or other early symptoms, cervical cancer has no telltale warning signs until it is so advanced that it is usually unresponsive to treatment. Only in the late stages does cervical cancer cause pain in the lower abdominal or back region, or produce other noticeable symptoms. Tests which provide early detection of cervical, uterine and vaginal cancer are paramount to the effective treatment and recovery film the disease. A Papanicolaou smear test, commonly referred to as a Pap test, has long been established as a highly usefull diagnostic tool which allows the identification of premalignant and malignant tissue at very early stages of the disease, as well as the identification of various inflamations and infections. The American Society of Clinical Pathologists recommends women have an annual Pap test.

A Pap test is a clinical procedure in which typically a bivalve speculum is inserted into a vaginal cavity and the cervix is exposed for sampling. A sample smear of cervical or vaginal secretions is then removed using an inserted scraper, probe, brush or similar type of device. The collected smear is evenly spread on one or more glass slides for microscopic examination. These standard-sized laboratory slides may be lined with hundreds of thousand of cervical cells. These slides are examined for the early detection of cancer or to determine the presence of certain hormonal conditions or certain infections. Lurking in these cells may be as few as a dozen abnormal cells. Finding such telltale cells is akin to finding a needle in a haystack, especially at the end of the day when laboratory technicians are likely to have examined countless Pap test slides. Therefore, the better the sampling, the better the chance of detecting an abnormal cell. In addition, abnormalities in cell shape may be slight and difficult for even the trained eye to detect, or may be masked by infection.

At one time Pap tests were performed almost exclusively by medical professionals in a doctor's office or a hospital. Many women, however, did not receive their yearly test because of their inability to visit a doctor on an annual basis, their reluctance to see a doctor or the expense of visiting a doctor coupled with test costs. As a result, self-administered sample collecting kits or system were developed so that women who did not go to the doctor on an annual basis could still be tested for abnormal cells. However, conventional self-administered sample collecting systems may not collect a sufficient amount of cervical tissue sample, or they may cause great discomfort to the user during use.

One such self-administered Pap test sampling collecting system is disclosed in U.S. Pat. No. 5,787,891 to Sak, that is herein incorporated by reference. This system includes a tubular speculum for inserting into the vaginal cavity, a guide sleeve located within the tubular speculum, and a swab assembly removably disposed within the guide sleeve. The swab assembly includes a sample collecting swab positioned within a swab sleeve in a retracted position when the device is first inserted into the vaginal cavity. A stem is then used for pushing the sample collecting swab out of the swab sleeve to an extended position and into contact with the cervical tissue. The sample collecting swab absorbs cervical samples until the user decides that enough sampling has been done.

Some patients may have difficulty using a self-administered sample collecting system because of the construction of its vaginal speculum. The speculum may be difficult or uncomfortable to insert into the vaginal cavity of the patient. The speculum may require the patient to use excessive force to push the speculum towards her cervix, thereby possibly causing an internal injury. Thus, the vaginal speculum may discourage women from taking the Pap test. Also, these self-administered sample collecting systems may not provide the user with the ability to determine the depth to which the vaginal speculum and the sampling device have been inserted into a vaginal cavity. The lack of proper insertion can lead to poor cervical samples and unreliable results.

Another problem that exists with conventional self-administered sample collecting systems for Pap tests is the inability of the patient to determine when a sufficient amount of sample has been obtained. These sampling systems do not effectively assist the patient in determining when the sampling device has been moved enough within the vaginal cavity to obtain an adequate amount of sample. Insufficient sampling may give inaccurate test results, increase costs and discourage a woman from receiving future testing at the recommended frequency.

Previous self-administered sample collecting systems require the patient to place the collected sample on medical examination slides. This procedure can produce an unsatisfactory specimen including bodily fluids that can impede the proper diagnosis of the smear. As a result, the patient will be forced to repeat the procedure in order to obtain another sample.

Thus, there is a need for an improved cervical sampling apparatus that can be effectively used by a woman performing sampling on herself. Further there is a need for an improved method of cervical sampling and a portable sampling system to advantageously provide for the detection of cancer.

It is an object of the present invention to overcome the aforementioned drawbacks in the conventional self-administered sample collecting systems for Pap tests.

An object of the present invention is to overcome the prior art problems of comfortably and effectively inserting a tubular speculum device into a vaginal cavity.

Another object of the present invention is to allow patients to readily determine when a sample collecting device has been rotated through a complete revolution so that the patient can keep an accurate count of how many times she has rotated the sample collecting device in order to achieve better sampling.

SUMMARY OF THE INVENTION

In view of the foregoing, the present invention is directed to an improved system for collecting samples of cervical tissue and/or vaginal secretions. In addition, the present invention is directed to an improved method of using the sample collecting system for a Pap test.

The present invention includes a cervical sampling apparatus that has a vaginal insertion tube, an introduction guide member that is removably positioned inside the vaginal insertion tube and a cervical sampler that can be inserted within the vaginal insertion tube after the introduction guide member has been removed. The cervical sampler can be slid and rotated relative to the vaginal insertion tube when positioned therein. The cervical sampler includes a sample collecting member for obtaining a cervical sample.

The present invention further includes a cervical sampling system that comprises a sampling system enclosure housing the cervical sampling apparatus and a cervical sample collection contains. The sample collection container is used to send the collected samples to a lab for testing.

The cervical sampling apparatus according to the present invention can also include the vaginal insertion tube having a signaling member and the cervical sampler including the sample collecting member, a handle, and an elongated body that extends along a longitudinal axis between the sample collecting member and the handle. The signaling member of the vaginal insertion tube cooperates with a signaling member of the cervical sampler to provide an audible or tactile signal to the user when the cervical sampler has been rotated past a reference point, thereby indicating that the cervical sampler has been rotated through a complete revolution.

In yet another aspect, the present invention includes an apparatus that can be positioned within a vaginal cavity. The apparatus includes a vaginal insertion tube and an introduction guide member for positioning within the vaginal insertion tube. The introduction guide member includes an elongated member and a guide head having a forward section that extends from the vaginal insertion tube when the introduction guide member is positioned within the tube. The forward section includes a substantially tapered conical area for introducing the vaginal insertion tube into the vaginal cavity. The guide head includes a passageway that extends through it and that is aligned with a passageway in the elongated member. These aligned passageways allow fluid within the vaginal cavity to pass through the introduction guide member in order to relieve pressure within the vaginal cavity.

The present invention also includes a method of performing cervical sampling that includes the steps of inserting the introduction guide member into the vaginal insertion tube so that a portion of the guide member extends outwardly from a forward end of the vaginal insertion tube, and introducing and advancing the vaginal insertion tube along with the inserted introduction guide member into a vaginal cavity. The introduction guide member is withdrawn from the vaginal insertion tube and the vaginal insertion tube is advanced further into the vaginal cavity until the vaginal insertion tube has reached a sampling position. Next, a cervical sampler including a sample collecting member is inserted into the vaginal insertion tube. The sample collecting member is extended from the vaginal insertion tube so that the sample collecting member contacts a portion of cervical tissue. A cervical sample is collected with the sample collecting member.

According to the present invention, the invention has many advantages, including providing an introduction guide member that operates with a vaginal insertion tube or speculum to reduce the pain and discomfort a patient may experience while obtaining cervical samples. The present invention also provides an insertion depth indicator including a tactile portion on the vaginal insertion tube that allows a patient to reliably determine the appropriate depth of the tube in order to reduce discomfort during its insertion.

The cervical sampler according to the present invention allows for a reduction of the number of components and the number of steps needed to collect a sample as compared to conventional sampling systems. The cervical sampler and sample collecting member according to the present invention reduce manufacturing costs and allows a patient to readily perform a sampling procedure without having to manipulate numerous, separately moving parts.

The signaling members allow the patient to count the number of revolutions that the sample collecting member has undergone by either audibly or tacitly indicating when a revolution has been completed. This features improves the previous sampling procedures by ensuring that better and more complete cervical samples are collected.

These and other objects, features and advantages of the present invention will be apparent upon consideration of the following detailed description thereon presented in connection with the following drawings in which like reference numerals identifying the elements throughout.

DETAILED DESCRIPTION OF THE PREFERRED EMBODIMENTS

Figure 1:
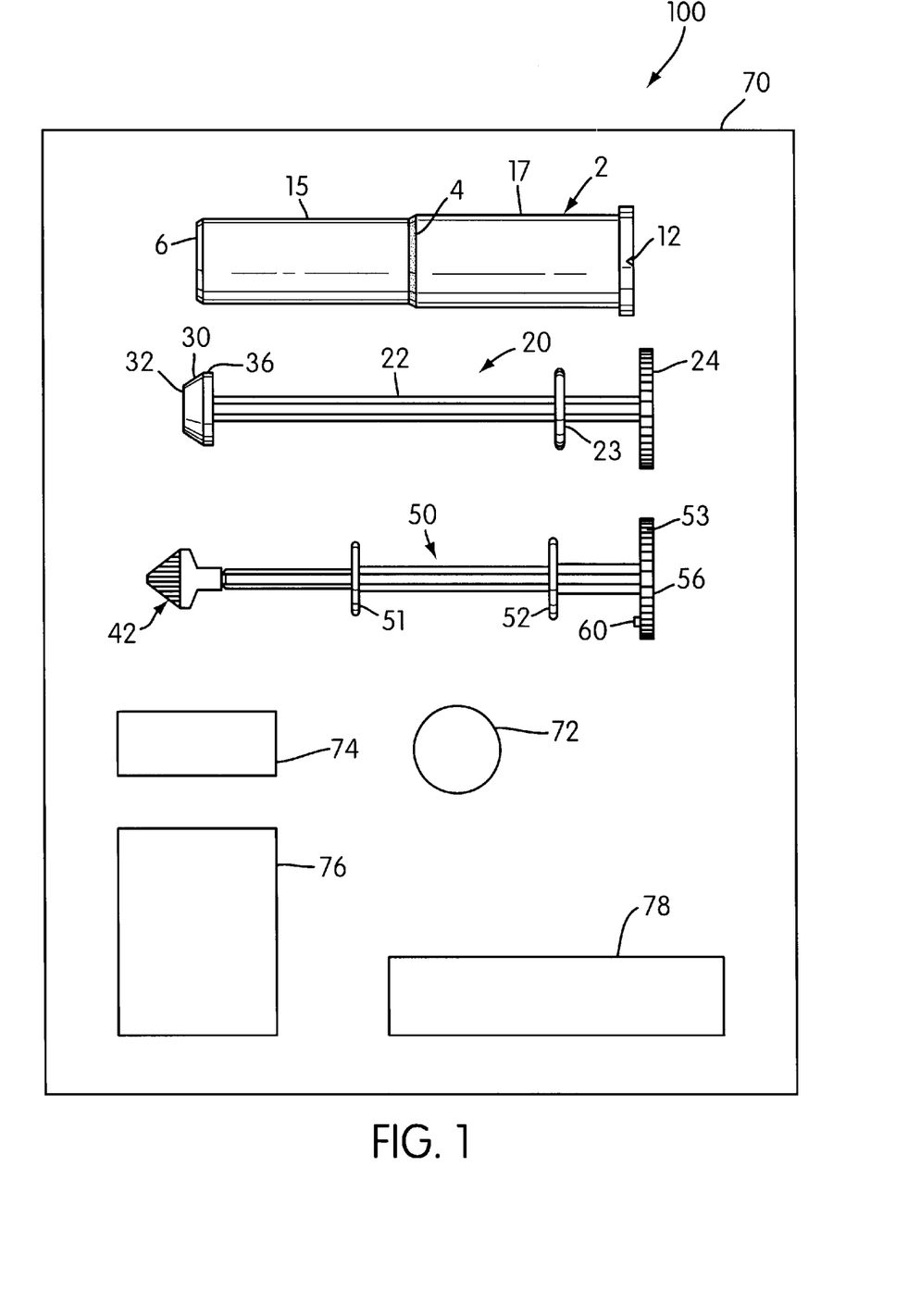
FIG. 1 is a plan view of a portable sampling system for obtaining cervical tissue in accordance to the present invention.

FIG. 1 illustrates a portable cervical tissue sample collecting system 100 for selfadministered sampling of cervical tissue and vaginal fluids. The sample collecting system 100 includes a vaginal insertion tube 2, an introduction guide member 20, a cervical sampler 50 including a sample collecting member 42, a collection container 72, a package of surgical lubricant 74, a pair of gloves 76, instructions for collecting samples, and transportation packaging materials 78 for the collected sample. These components of the system 100 are packaged within a single container 70 or other suitable enclosure. In this manner, the sample collecting system 100 will be easily handled by retailers, consumers, and public heath organizations and can be individually mailed to patients who are unable or unwilling to visit a doctor. The enclosure 70 will also maintain the sterility of the various components of the portable sampling system.

Referring to FIGS. 1–8, an overview of a manner of operating the sample collecting system 100 in accordance with the present invention follows. A pre-insertion assembly 10 is formed by placing the introduction guide member 20 within the vaginal insertion tube 2. The assembly 10 is then inserted into a patient after she assumes a predetermined desired position. Once the insertion tube 2 has been inserted to an appropriate depth, such as the midpoint of the total insertion distance, the introduction guide member 20 is removed from the vaginal insertion tube 2. The advancing of tube 2 is continued until it is positioned within the vaginal cavity at a sampling position where the front end 6 of the vaginal insertion tube 2 is located immediately in front of the cervix. The cervical sampler 50 is then inserted into the vaginal insertion tube 2. The sample collecting member 42 is pushed into contact with cervical tissue, and a cervical tissue sample is collected by rotating the cervical sampler 50. The cervical sampler 50 is then removed from the vaginal cavity and the cervical tissue sample is transferred from the sample collecting member 42 to the collection container 72 that retains a preservative solution. The collection container 72 is packaged and sent to a predetermined laboratory for analysis. After the sample has been analyzed, the results can be communicated back to the patient.

Figure 2:
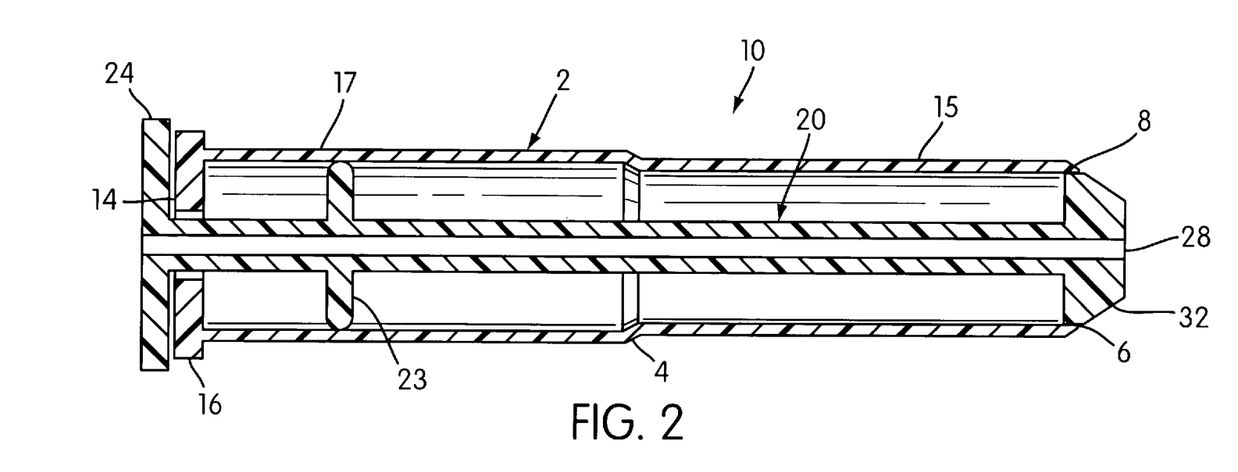
FIG. 2 is a cross section of a tubular speculum and an introduction guide member in accordance with the present invention.
Figure 3:
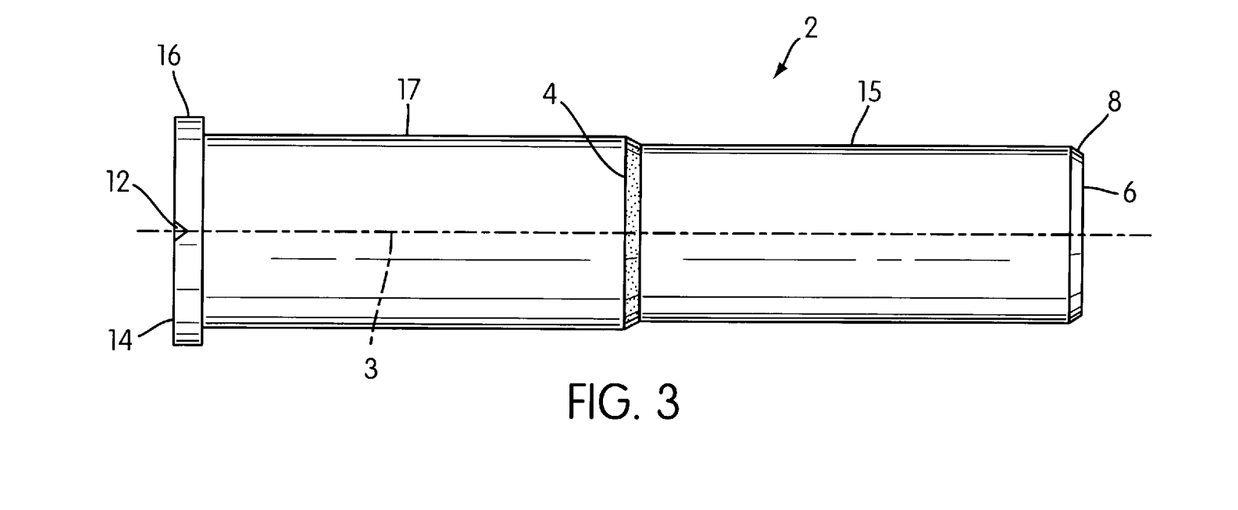
FIG. 3 is a side view of the tubular speculum constructed in accordance with the present invention.

Referring to the drawings, there is illustrated in FIG. 2, the vaginal insertion tube 2 and the introduction guide member 20 in a pre-insertion assembly 10. FIG. 3 illustrates the vaginal insertion tube 2, such as a tubular speculum, for opening the vaginal cavity of a patient and providing a passageway in order to collect a cervical tissue sample. The vaginal insertion tube 2 includes a front end 6, an insertion position indicator 4, a rear end 14, an indicator member 12 and a center axis 3. In a preferred embodiment, the vaginal insertion tube 2 also includes a forward cylinder section 15 and a rear cylinder section 17. The forward cylinder section 15 includes the front end 6 having a tapered edge 8 which extends outward and rearward from an inner surface of the leading edge of the tube 2. The forward cylinder section 15 has an inner diameter of between 1.0 and 1.25 inches, preferably about 1.125 inches and an outer diameter between 1.125 and 1.375 inches, preferably 1.25 inches. The rear cinder section 17 has an inner diameter of between 1.15 and 1.35 inches, preferably 1.219 inches, and an outer diameter between 1.30 and 1.60 inches, preferably 1.41 inches. The variance in outer diameters between cylinder sections 15 and 17 provides for an advantageous structure to perform the cervical sampling.

The rear cylinder section 17 includes the rear end 14 of the vaginal insertion tube 2 having a flange 16, and the indicator member 12, such as a rotator cuff groove or notch portion which extends along the circumference of the rear end about 0.125 inch. However, the indicator member 12 can extend different distances along the end 14. The indicator member 12 operates in conjunction with a small protuberance portion 60, such as a rotator cuff, on the handle 56 of the cervical sampler 50 as discussed below. The indicator member 12 and protuberance portion 60 provide an audible and tactile indication each time the user rotates the cervical sampler 50 through a complete revolution and past a reference point. In another embodiment, the tube 2 can be one cylindrical section having constant outer and inner diameters throughout its length The tube 2 also includes an insertion position indicator 4 having a tactile portion around its outer circumference. The insertion position indicator 4 allows the patient to easily and reliably determine the appropriate depth to insert the vaginal insertion tube 2. The insertion position indicator 4 may include any surface discontinuity such as a surface depression, a step between the forward cylinder section 15 and the rear cylinder section 17, as shown in FIG. 3, or a variance in surface texture on the surface of the tube 2. In a preferred embodiment, the insertion position indicator 4 is located at one-half the length of the tube 2 to indicate the midpoint of the insertion depth. This feature advantageously allows the patient to better judge the depth of insertion into the vaginal cavity by alerting her when half of the tube 2 has been inserted. In addition, the insertion position indicator 4 provides the user with a predetermined time for removing the introduction guide member 20; when the position indicator 4 is proximate to the vaginal walls, the guide member 20 is removed from the vaginal insertion tube 2 and the tube 2 is advanced until located in a sampling position in front of the cervix. Further the insertion position indicator 4 allows the patient to feel the location of the tube relative to the outer tissue of the vagina.

Figure 4:
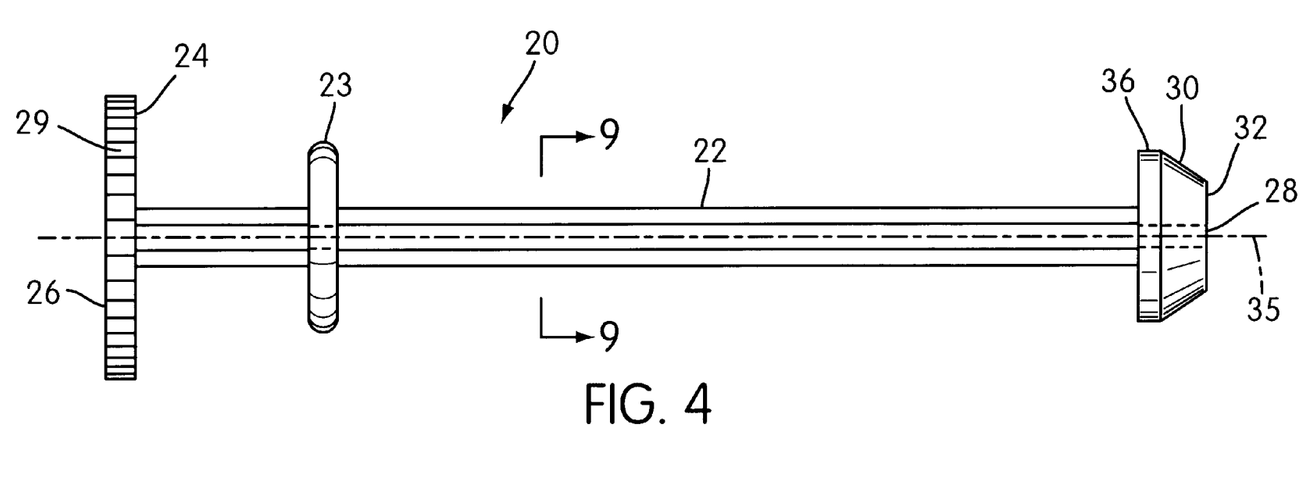
FIG. 4 is a side view of the introduction guide member construction in accordance with the present invention.
Figure 9:
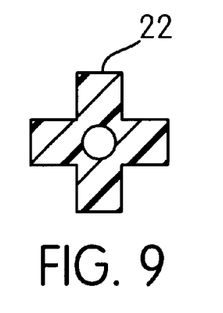
FIG. 9 is a cross section of an elongated member of the introduction guide member taken along line 9—9 of FIG. 4.

The introduction guide member 20, that assists in distending the vaginal cavity, is illustrated in FIGS. 2, 4 and 9. The introduction guide member 20 preferably includes a guide head 32, an elongated member 22, a support member 23, and a handle 24 at a rear end 26. The guide head 32 includes a tapered-edge nose cone portion 30 integrally formed with a cylinder portion 36. A first leading edge of the beveled nose cone portion 30 is preferably flat so that the user will not be injured by a sharp or pointed edge during insertion. The nose cone portion 30 includes a taper which is generally aligned with tapered edge 8 of tube 2 to create a sufficiently smooth transition between these elements and provide for comfortable and easy insertion of the introduction guide member 20 into the vaginal cavity. The taper of the tapered edge 8 and guide head 32 may range from 25 to 45 degrees relative to the outer surface of the tube 2. In a preferred embodiment, the tapered edge 8 and guide head 32 are at approximately 30 degrees to an axis extending parallel to the longitudinal axis 3 of the tube 2. The nose cone portion 30 and cylinder portion 36 are preferably one solid piece formed of plastic material. The guide head 32 preferably has a diameter, about 1.10 inches, which is slightly smaller than the interior diameter of the vaginal insertion tube 2 to allow the introduction guide member 20 to slide, and rotate, if desired, within the vaginal insertion tube 2. A penetrating tubular opening 28 extends through the nose cone portion 30 and the cylinder portion 36 to create a passageway for fluids to pass through the guide head 32 during insertion. The elongated member 22 extends between the guide head 32 and the handle 24 and is aligned with the guide head 32 along the center axis 35 of the introduction guide member 20. A passageway may be formed in the elongated member 22 and aligned with the tubular opening 28 to allow fluids to pass through the guide head 32 and out of the assembly 10. This feature allows for easier insertion of the vaginal insertion tube 2 by reducing pressure in the vaginal cavity as a result of providing an open, fluid escape passageway from the forward face of the guide head 32 to the trailing face of the rear end 26 which permits fluid to exit the vaginal cavity through the introduction guide member 20. Referring to FIG. 9, the elongated member 22 includes a generally "X" shaped cross section which assists in providing it with structural stability and resistance to excessive torsional deformation. However, other well-known structurally stable cross sections can be used.

In a preferred embodiment, the introduction guide member 20 includes at least one disk shaped support member 23 integrally formed with the elongated member 22. The support member 23 assists in providing lateral stability to the introduction guide member 20 and assists in aligning the guide member 20, when the guide member 20 is inserted into the vaginal insertion tube 2. In another embodiment, the cylinder portion 36 of the guide head 32 may be extended towards the rear end 26 so that the support member 23 is not needed. The length of the cylinder portion 36 would be sufficient to provide stability and alignment of the introduction guide member 20 within the tube 2. In this embodiment, the length of the cylinder portion may be between 1 to 1.50 inches along the length of the elongated member 22.

The rear end 26 of the introduction guide member 20 preferably includes a handle 24 that allows the patient or user to insert and remove the introduction guide member 20 from the vaginal insert on tube 2. In a preferred embodiment, the handle 24 is in the shape of a disk having a forward face of the disk integrally connected to the elongated member 22, and a diameter larger than the diameter of the flange 16 of the vaginal insertion tube 2. If desired, the handle 24 may be in any shape such as a rectangle or a cylinder. The handle 24 preferably includes of a tactile portion 29 such as, a straight knurling pattern on the outer edge around the circumference of the disk. This feature provides an advantageous surface to assist the user in grasping and operating the introduction guide member 20. The handle 24 also preferably serves a dual function as a stopping member for the introduction guide member 20. The handle 24 stops motion in the axial direction when the patient fully inserts the introduction guide member 20 into the vaginal insertion tube 2. By the handle 24 stopping the motion of the guide member 20 at its extended position, the guide head 32 of the introduction guide member 20 preferably has the nose cone portion 30 extending axially away from the front end 6 and substantially aligned with the tapered edge 8 of the vaginal insertion tube 2 for creating a substantially continuous tapered region that provides for comfortable insertion of the tube 2.

The vaginal insertion tube 2 is preferably constructed from a transparent plastic material, such as a high impact polystyrene (HIPS) crystal. The introduction guide member 20 is constructed preferably from a filled plastic material such as, polypropylene with a calcium carbonate mineral filler. Transparent plastic materials assist the patient in understanding how the vaginal insertion tube 2, introduction guide member 20, and cervical sampler 50 operate, which is an important consideration since the system 100 may be used by a woman with little or no medical training. The plastic material for the vaginal insertion tube 2 and introduction guide member 20 should be preferably lightweight, biocompatible, inert, capable of being sterilized and have a generally smooth surface so they will not injure the user. The plastic material should also be relatively inexpensive so that the production costs are kept low and the system 100 remains affordable. The vaginal insertion tube 2 is preferably an approximate 6.5 inches (16 centimeters) in length. Also, the introduction guide member 20 is preferably an approximate 6.81 inches (17.3 centimeters) in length. Other dimensions, however, may used.

The vaginal insertion tube 2 and the introduction guide member 20 are preferably manufactured or formed in a process such as, injection molding. The components of the introduction guide member 20, e.g, the elongated member 22, support member 23, handle 24, and guide head 32 with integral nose portion 30 and cylinder portion 36, should be formed with a similar process. A change in the surface texture of the vaginal insertion tube 2 can be formed by a process such as scoring, routing or sanding the outer surface of the tube 2. The processes create a groove, a series or pattern of grooves, surface texture variance, or other types of marks on vaginal insertion tube 2 that a patient can feel with their hands during the insertion of the vaginal insertion tube 2.

Figure 5:
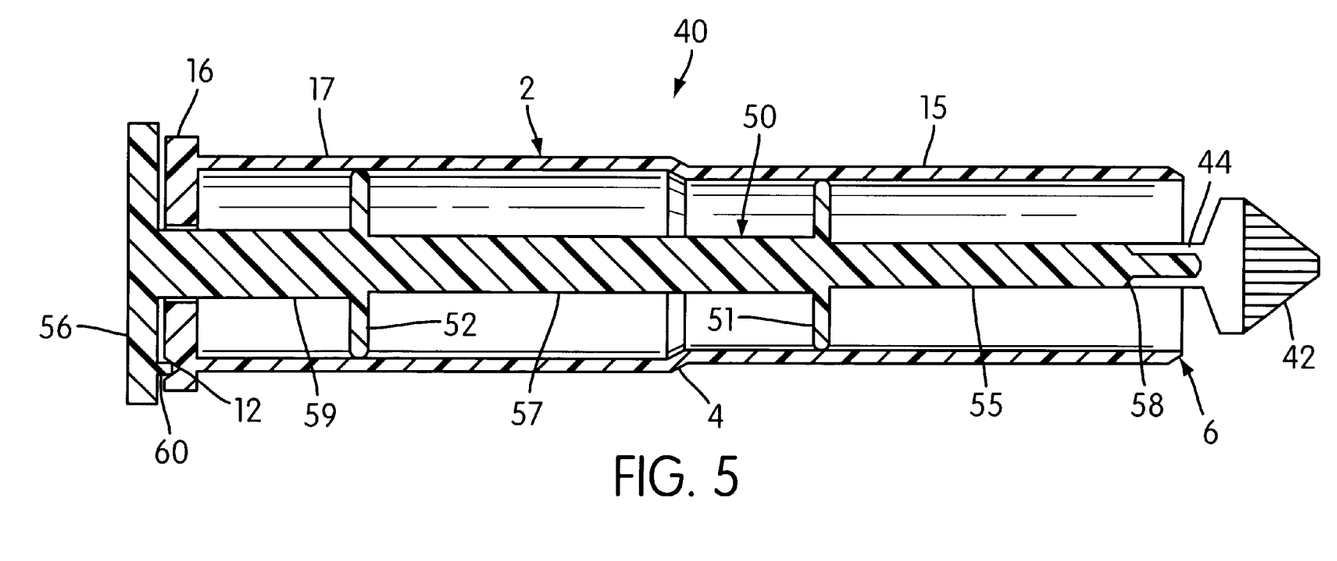
FIG. 5 is a cross section of the tubular speculum and a cervical sampler that includes a sample collecting member according to the prevent invention.

FIGS. 5 illustrates the cervical sampler 50 and the vaginal insertion tube 2 in an assembled position 40. The cervical sampler 50 constructed in accordance with the present invention is illustrated in FIGS. 5–8. The cervical sampler 50 includes a sample collecting member 42 that comes into contact with tissue of the cervix. The sample collecting member 42 removes cervical tissue cells that will be analyzed after the sample collection process has been completed. Referring to FIG. 5, the sample collecting member 42, in a preferred embodiment, includes a cervical brush used in gynecological procedures that samples a transformation zone of a cervix, such as the endocervix and ectocervix. The brush is preferably flexible and designed with many extensions or bristles to collect cervical cells. Brushes which can be used are similar to those manufactured by Wallach Surgical Devices. The sample collecting member 42, however, may include any type of brush, probe, or the like which can similarly be used in gynecological cytology to collect a cervical cell specimen. In a preferred embodiment, the sample collection member 42 is utilized for an automated or computer assisted Pap test cytological analysis. The sample collecting member 42 should be preferably smaller in width than the inner diameter of the vaginal insertion tube 2 to allow the cervical brushto fit inside the tube 2.

Figure 6:
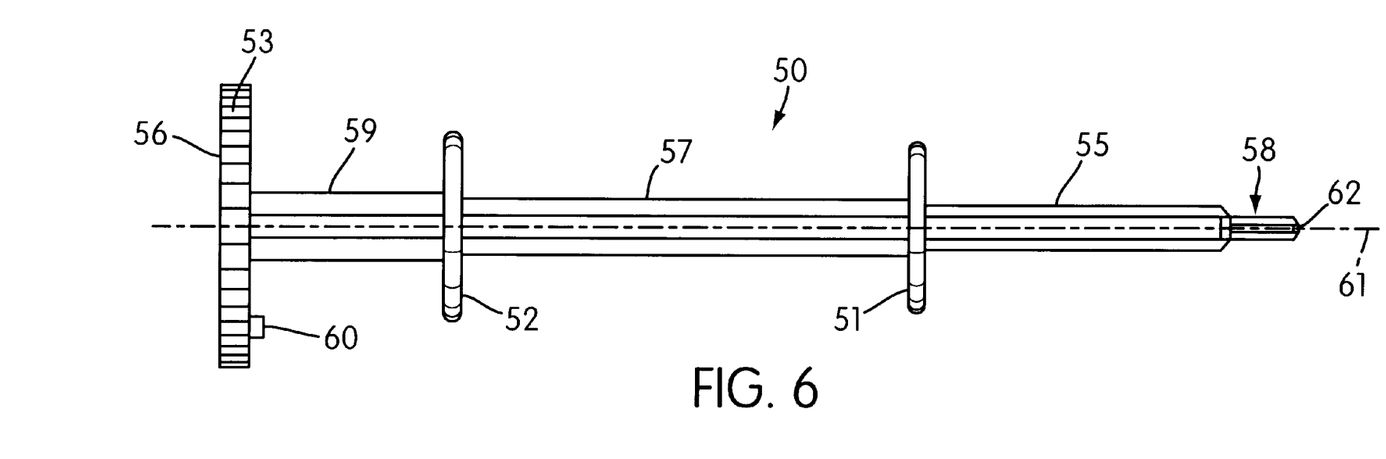
FIG. 6 is a side view of the cervical sampler of FIG. 5 without the sample collecting member in accordance with the present invention.

The cervical sampler 50 includes a holding end 58, alignment members 51, 52, an elongated body in three sections 55, 57, 59, and an integral disk handle 56. The forward 51 and rear 52 alignment members are used to guide and to align the cervical sampler 50 along the center longitudinal axis 3 of the vaginal insertion tube 2. As shown in FIGS. 5–6, the alignment members 51, 52 move relative to the insertion tube 2, rather than being fixed to the tube 2. As best shown in FIG. 5, the alignment members 51, 52 are integrally formed with and connected to the elongated body as a single unit. The alignment members 51, 52 are also positioned perpendicular to the longitudinal axis 61, such that the alignment members 51, 52 move in conjunction with the elongated body whenever the body slides or rotates within the vaginal insertion tube 2. Also, the alignment members 51, 52 are preferably formed in the shape of a disk and may have the same or different diameters. The diameter of the forward alignment member 51 is preferably smaller than the diameter of the rear alignment member 52, in order to contact the diameter of the corresponding section of the vaginal insertion tube 2. In a preferred embodiment, the sections of elongated body 55, 57, 59 each have the shape of an "X" or a cross structure. The thickness of the elongated body varies from section to section. The forward section 55 extending between the holding end 58 and the forward alignment member 51 has a constant outer thickness of about 0.25 inches which is measured between the outer surfaces of the legs of the cross. The middle section 57 extending between the forward alignment member 51 and the rear alignment member 52 has a constant thickness of about 0.375 inches which is larger than the thickness of the forward section 55. Similarly, the rear section 59 extending between the handle 56 and the rear alignment member 52 has a constant thickness of about 0.50 inches which is larger than that of the middle section 57. This variance of thickness of the elongated body preferably provides for better resistance to torsional deformation at the rear section 59 and a more stable structure when handle 56 is rotated and the protuberance portion 60 on the handle 56 contacts the indicator member 12. If desired, other shapes of the elongated body may be utilized, such as a rectangle or cylinder. In addition, the elongated body may be formed as a single constant thickness rod extending between the holding end 58 and the handle 56.

Figure 7:
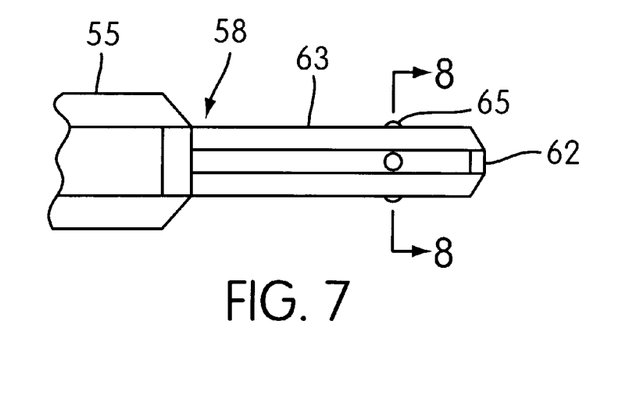
FIG. 7 is a side view of a forward end of the cervical sampler shown in FIG. 6.
Figure 8:
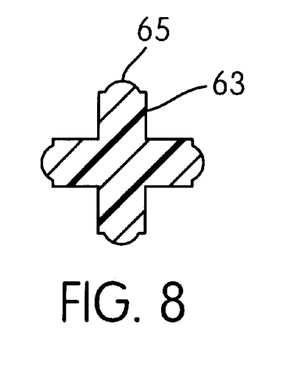
FIG. 8 is a cross section of the forward end shown in FIG. 7 taken along line 8—8 in FIG. 7.

The holding end 58 of the cervical sampler 50 includes a holder 62 that extends axially outward from the holding end 58, and mates with a complimentarily formed internal cavity 44 of the sample collecting member 42. Referring to FIGS. 7–8, the holder 62 includes an elongated protuberance, with a generally symmetrical "X" shape cross section that is integrally formed with the forward section 55 of elongated body and extends therefrom. This holder 62 supports the sampling collecting member 42, while eliminating additional parts used in previous devices. The "X" or cross shape of the holder 62 includes a plurality of arms 63. In a preferred embodiment, the arms 63 include hemispherical protuberances 65 that engage corresponding surfaces within the internal cavity 44 of the sample collecting member 42. This engagement improves the transfer of rotational motion of the disk handle 56 to the sample collecting member 42. The mating of the holder 62 and the sample collecting member 42 also creates a frictional contact between the surfaces of complimentary internal cavity 44 of the sample collecting member 42 and the cross structure. The plurality of hemispherical protuberances 65 advantageously increases this frictional contact. The "X" or cross structure also allows the sample collecting member 42 to slide in conjunction with the corresponding movement of the elongated body. In a preferred embodiment, the sample collecting member 42 is removable from the holder 62 at the holding end 58.

Referring FIG. 6, at the rear end of the cervical sampler 50, a center of the disk handle 56 is integrally connected to the rear section 59 of the elongated body. In a preferred embodiment, the disk handle 56 extends radially and perpendicularly from the longitudinal axis 61, and includes a tactile portion 53, such as a straight knurling pattern. The disk handle 56 performs several functions. First, the disk handle 56 can be grasped by the patient in order to insert and remove the cervical sampler 50 from the vaginal insertion tube 2. In this manner, the disk handle 56 controls how far the sample collecting member 42 will extend from vaginal insertion tube 2. Second, the disk handle 56 is of sufficient size to allow the patient to grasp the handle 56 and freely rotate the cervical sampler 50 within the vaginal insertion tube 2 and correspondently rotate the sample collecting member 42 extending outside the tube 2, in order to collect the necessary cervical cell sample. In a preferred embodiment, the handle 56 has a diameter larger than that of the vaginal insertion tube 2. Third, in a preferred embodiment, the handle 56 includes the protuberance portion 60, such as a rotator cuff, having a forward extending protuberance that cooperates with the indicator member 12 to create an audible or tactile indication of the completion of a revolution. This indication or signal occurs when the user rotates the protuberance portion 60 past a reference point such as the indicator member 12 during the sampling procedure. The protuberance portion 60 extends from the forward face of the handle 56 in the direction of the sample collecting member 42. The protuberance portion 60 substantially contacts the indicator member 12, such that the audible or tactile indication is produced and communicated to the user.

Referring to FIG. 6, the forward 55, middle 57, and rear 59 sections of the elongated body, the alignment members 51, 52 and the handle 56 are preferably constructed from a plastic material, such as polypropylene having a calcium carbonate filler. Injection molding is a preferred manufacturing process used to form the above mentioned components. The plastic material should be preferably lightweight, relatively inexpensive, capable of being sterilized, biocompatible, inert and have a generally smooth surface.

The cervical sampling apparatus in accordance with the present invention may be used in the following manner. The patient or user fully inserts the introduction guide member 20 into the vaginal insertion tube 2 to form the pre-insertion assembly 10 shown in FIG. 2. The patient substantially aligns the guide head 32 with the tapered edge 8 to allow the nose cone portion 30 to extend outward from the edge 8. Also the patient applies a portion of sterile surgical lubricant 74 to the guide head 32 of the introduction guide member 20 and if desired, the tapered edge 8 of the vaginal insertion tube 2. The patient also performs a maneuver, on a substantially horizontal surface, by lying down on her back with her knees bent upward (a modified situp position) in which the pelvic floor of the patient is depressed. This maneuver advantageously allows the cervix to align with the tube 2 due to the added effect of creating abdominal pressure during the insertion of the introduction guide member 20 and vaginal insertion tube 2, coupled with the depression of the pelvic floor.

Next, the patient slowly inserts the introduction guide member 20 and vaginal insertion tube 2 into the vagina in order to distend the vaginal cavity and align the axis of the tube 2 with the cervix of the patient. The introduction guide member 20 and vaginal insertion tube 2 are advanced together until the insertion depth indicator 4 is proximate the vaginal walls. When the midpoint depth is reached, the introduction guide member 20 is withdrawn from the vaginal insertion tube 2 which-helps reduce the potential for guide member 20 to contact and injure the cervix. During the removal of the guide member 20, the patient retains the position of the tube 2 in the vaginal cavity. After the introduction guide member 20 is removed, the patient further advances the tube 2 into the vaginal cavity until the tube 2 is in a sampling position at the cervix and resistance is felt by the patient. Referring to FIG. 5, the position of the vaginal insertion tube 2 is maintained and the patient inserts the cervical sampler 50 into the tube 2. As discussed above, the alignment members 51, 52 align the center of the sample collecting member 42 with the center axis 3 of the vaginal insertion tube 2 and the cervix.

The patient then applies pressure to the cervical sampler 50 thereby contacting a portion of the cervix with the sample collecting member 42. Next, the patient maintains the position of the vaginal insertion tube 2 and rotates the handle 56 between 5 and 15 complete revolutions—as indicated by the indicator member 12, such as a groove portion, and protuberance portion 60. Depending on brush designs more or less rotations could be employed. In a preferred embodiment, the handle 56 is rotated through ten (10) complete revolutions. In turn, the sample collecting member 42 will also be rotated ten revolutions so as to collect cervical samples. The indicator member 12 and protuberance portion 60 reliably permit the patient to determine when a rotation has been completed. This feature is advantageous to determining the amount of cervical sample collected. In a preferred embodiment, when the indicator member 12 contacts protuberance portion 60, an audible signal is produced which signals the patient that a revolution of the cervical sampler 50 has been completed. Likewise, if a patient has difficulty in determining the audible signal, the feature can also provide a tactile signal, such as vibrating of the indicator member 12 or contacting a finger of the user as the cervical sampler 50 completes each full revolution. The audible and tactile signaling feature is advantageous because the patient is laying on her back, holding the vaginal insertion tube 2 in one hand and with the other hand turning or rotating the cervical sampler 50, therefore, she cannot see or will have difficulty seeing when a complete revolution has been accomplished.

In a preferred embodiment, after the appropriate number of rotations, such as ten, the proper amount of cervical sample has been collected. The patient removes the cervical sampler 50 from the vaginal insertion tube 2, and subsequently withdraws the vaginal insertion tube 2 from the vaginal cavity. In a preferred embodiment, the sample collection portion 42 is then removed from the remainder of the cervical sampler 50 and placed into the collection container 72, such as a vial, that retains an ethanol based liquid thin layered preservative solution used in gynecological cytology, such as AutoCyte PREP. This method advantage allows for using substantially automated screening of the cervical sample to reduce the diagnosis problems associated with a manual method of screening. Alternatively, the sample collecting member 42 is not released from the holder 62 and placed in the collection container 72. Instead, the sample collecting member 42 remains connected to elongated body forward section 55 and is swirled, agitated, or washed in a container 72 including a methanol based preservative solution to remove the cervical cells. In general, the above preservative solutions provide for preservation of cervical cells for future analysis in gynecological cytology. Once the sample is collected, the collection container 72 is sealed, labeled and transported to a predetermined laboratory for analysis. In a preferred embodiment, the laboratory includes automated or computer assisted diagnosis equipment for analysis of the cervical sample collected by the patient. After the cells have been transferred to the solution or analyzed, the sample collecting member 42 may discarded. Once the laboratory completes the analysis of the cervical sample, the results are communicated back to the patient. The diagnostic testing procedures do not form part of this invention.

While these particular embodiments of the invention has been shown and described, it is recognized the various modifications thereof will occur to those skilled in the art. Therefore, the scope of the herein-described invention shall be limited solely by the claims appended hereto.

What is claimed is:

1. A cervical sampling apparatus, comprising:
   a vaginal insertion tube;
   an introduction guide member for being removably positioned within the vaginal insertion tube, the introduction guide member having a guide head extending beyond an end of the tube when inserted therein for guiding the vaginal insertion tube into a vaginal cavity; and
   a cervical sampler for being slidably and rotatably disposed in the vaginal insertion tube after the introduction guide member is removed from the vaginal insertion tube, the cervical sampler including a sample collecting member for obtaining a cervical sample when positioned within the vaginal cavity.

2. The apparatus of claim 1, wherein an insertion position indicator is located along a length of the vaginal insertion tube.

3. The apparatus of claim 2, wherein the insertion position indicator includes a discontinuity along the vaginal insertion tube that can be felt by a user.

4. The apparatus of claim 1, wherein the cervical sampler includes an elongated member having a forward section and a rear section, the forward section being connected to a holder for mating with the sample collecting member and having an outer diameter, and the rear section being secured to a handle for grasping by an operator and having an outer diameter which is greater than the diameter of the forward section.

5. The apparatus of claim 4, wherein the holder mates with the sampling collecting member such that the sample collecting member rotates when the handle is rotated.

6. The apparatus of claim 4, wherein the cervical sampler further includes at least two alignment members which align the cervical sampler with a longitudinal axis of the vaginal insertion tube when the cervical sampler is positioned within the vaginal insertion tube.

7. The apparatus of claim 6, wherein the alignment members are integrally formed with an elongated portion of the cervical sampler.

8. The apparatus of claim 4, wherein the vaginal insertion tube includes a signaling member for cooperating with a signaling member of the cervical sampler to indicate to the user when the handle has been rotated past a reference point.

9. The apparatus of claim 8, wherein the signaling member of the cervical sampler includes a protuberance.

10. The apparatus of claim 8, wherein the signaling member of the vaginal insertion tube includes a notch.

11. The apparatus of claim 1, wherein the introduction guide member includes a forward end and a rear end, the forward end of the introduction guide member having the guide head including a tapered portion, the rear end of the introduction guide member having a stop member.

12. The apparatus of claim 11, wherein the tapered portion of the guide head is substantially aligned with a tapered edge of the vaginal insertion tube for creating a substantially continuous tapered surface.

13. The apparatus of claim 11, wherein the guide head of the introduction guide member includes an elongated inner passageway for allowing fluid from the vaginal cavity to enter the guide head.

14. The apparatus of claim 13, wherein the introduction guide member further includes an elongated member extending between the guide head and the rear end, the elongated member having an internal passageway aligned with the passageway in the guide head for allowing fluid to exit the vaginal cavity through the introduction guide member.

15. The apparatus of claim 1, wherein the sample collecting member includes a cervical sample brush.

16. A cervical sampling system, comprising:
   (a) a sampling system enclosure;
   (b) a cervical sampling apparatus disposed within the sampling system enclosure, the cervical sampling apparatus including:
      (1) a vaginal insertion tube having a leading end for being inserted into a vaginal cavity,
      (2) an introduction guide member for being removably positioned within the vaginal insertion tube, the introduction guide member including a forward portion for extending beyond the leading end of the tube when inserted therein for guiding the vaginal insertion tube into the vaginal cavity; and
      (3) a cervical sampler for being slidably and rotatably disposed in the vaginal insertion tube after the introduction guide member is removed from the vaginal insertion tube; the cervical sampler including a sample collecting member for obtaining a cervical sample when positioned within the vaginal cavity; and
   (c) a cervical sample collection container.

17. The system of claim 16, wherein the vaginal insertion tube includes an insertion depth indicator which has a surface discontinuity located at substantially a mid-point of a length of the tube.

18. The system of claim 17, wherein the sample collection container includes a liquid solution.

19. The system of claim 18, further comprising packaging for use when forwarding the sample collection container to a location so that collected samples can be analyzed.

20. The system of claim 16, wherein the vaginal insertion tube includes a signaling member for cooperating with a signaling member of the cervical sampler to indicate to the user when the cervical sampler has been rotated past a reference point.

21. The system of claim 20, wherein the signaling member of the vaginal insertion tube causes an audible signal to be produced when it contacts the signaling member of the cervical sampler.

22. The system of claim 16, wherein the cervical sampler further includes at least two alignment member which align the cervical sampler with a longitudinal axis of the vaginal insertion tube when the cervical sampler is positioned within the vaginal insertion tube.

23. The system of 22, wherein the alignment members are integrally formed with an elongated portion of the cervical sampler.

24. The system of claim 16, wherein the introduction guide member includes, an elongated member, a guide head having a forward tapered portion, and an internal passageway that extends between a forward end of the guide head and a rear end of the elongated member for allowing fluids to exit the vaginal cavity through the introduction guide member.

25. Method of obtaining cervical samples, comprising the steps of
   a) inserting an introduction guide member into a vaginal insertion tube so that a portion of the introduction guide member extends outwardly from a forward end of the vaginal insertion tube;
   b) introducing and advancing the vaginal insertion tube along with the inserted introduction guide member into the vaginal cavity;
   c) withdrawing the introduction guide member from the vaginal insertion tube;
   d) advancing the vaginal insertion tube further into the vaginal cavity after withdrawing the introduction guide member until the vaginal insertion tube has reached a sampling position;
   e) inserting a cervical sampler including a sample collecting member into the vaginal insertion tube;
   f) extending the sample collecting member into the vaginal cavity from an end of the vaginal insertion tube;
   g) contacting a portion of cervical tissue within the vaginal cavity with the sample collecting member, and
   h) collecting a cervical sample with the sample collecting member.

26. The method of claim 25, further comprising the step of coating the introduction guide member with a surgical lubricant.

27. The method of claim 25, further comprising the steps of removing the sample collecting member from a holder portion of the cervical sampler and placing the sample collecting member in a collection container.

28. The method of claim 25, wherein the step of inserting the cervical sampler includes substantially maintaining the vaginal insertion tube within the vaginal cavity at the sampling position.

29. The method of claim 25, wherein the step of withdrawing the introduction guide member from the vaginal insertion tube further includes substantially maintaining the position of the vaginal insertion tube as the introduction guide member is withdrawn.

30. The method of claim 25, further comprising the step of advancing the vaginal insertion tube and the inserted introduction guide member into the vaginal cavity until a mid-point of the vaginal insertion tube is substantially proximate a wall of the vaginal cavity.

31. The method of claim 25, further comprising the step of substantially washing the sample collecting member in a solution inside of a collection container to remove cervical cells from the sample collecting member.

32. The method of claim 25, further comprising the step of positioning a patient on a substantially horizontal surface with the knees of the patient bent upward in a sit up position that places pressure on an abdomen and depresses a pelvic floor of the patient.

33. The method of claim 25, wherein the step of collecting a cervical sample with the sample collecting member includes rotating the sampling collecting member at least ten complete revolutions.

34. A cervical sampling apparatus for collecting a cervical tissue sample, comprising:
   a vaginal insertion tube having a signaling member; and
   a cervical sampler that is slidably and rotatably disposed within the vaginal insertion tube, the cervical sampler having a sample collecting member, a handle, and an elongated body with a longitudinal axis extending between the sample collecting member and the handle, the handle extending at an angle to the longitudinal axis and having a signaling member; the sample collecting member engaging the elongated body so that the sample collecting member slides and rotates with corresponding movement of the handle, and wherein the signaling member of the vaginal insertion tube cooperates with the signaling member of the cervical sampler to provide a signal to the user when the cervical sampler has been rotated past a reference point.

35. The apparatus of claim 34, further comprising at least two alignment members extending perpendicular to the longitudinal axis of the elongated body for contacting the vaginal insertion tube, the alignment members being integrally formed with the elongated body so that they rotate and slide with corresponding movement of the handle.

36. The apparatus of claim 35, wherein each alignment member includes a circular disk and the elongated body includes a forward section having an outer diameter and a rear section having an outer diameter which is greater than the outer diameter of the forward section.

37. The apparatus of claim 35, wherein the signaling member of the vaginal insertion tube and the signaling member of the cervical sampler produce an audible signal when they contact each other.

38. The apparatus of claim 35, wherein the signaling member of the vaginal insertion tube and the signaling member of the cervical sampler produce a tactile signal when they contact each other.

39. The apparatus of claim 34, wherein a forward end of the elongated body includes a cross-shaped protuberance that is positioned within a complementary mating cavity of the sample collecting member so that the sample collecting member rotates when the elongated body rotates.

40. The apparatus of claim 34, wherein the vaginal insertion tube includes an insertion depth indicator with a tactile portion positioned on an exterior surface of the tube.

41. An apparatus for being positioned within a vaginal cavity comprising:

a vaginal insertion tube for positioning within a vaginal cavity; and an introduction guide member for positioning within the vaginal insertion tube, the introduction guide member including an elongated member and a guide head having a forward section for extending from the vaginal insertion tube when the introduction guide member is positioned therein, the forward section including a substantially tapered outer surface for introducing the vaginal insertion tube into the vaginal cavity, the guide head including a passageway extending therethrough, the passageway being aligned with a passageway in the elongated member for allowing fluid within the vaginal cavity to pass through the introduction guide member in order to relieve pressure within the vaginal cavity.

42. The apparatus of claim 41, wherein the forward section of said guide head includes a truncated cone and the elongated member includes a support member.

43. The apparatus of claim 41, wherein the vaginal insertion tube includes a tapered edge for aligning with the tapered outer surface of the guide head to form a substantially continuous tapered region.

44. The apparatus of claim 41, wherein the vaginal insertion tube includes an insertion depth indicator having a surface discontinuity located along the length of the tube.

45. The apparatus of claim 44, wherein the surface discontinuity includes a step along an outer surface of the insertion tube.

46. The apparatus of claim 44, wherein the surface discontinuity includes a variance in an outer surface texture of the vaginal insertion tube.

47. The apparatus of claim 41, wherein a rear end of the introduction guide member has a stop member.

* * * * *